(12) United States Patent
Horgan et al.

(10) Patent No.: US 8,759,464 B2
(45) Date of Patent: Jun. 24, 2014

(54) POLAR, MULTI-HYDROXYL FUNCTIONAL AMINO COMPOUNDS, COMPOSITIONS, PROCESS FOR PREPARATION, THEIR USES AND APPLICATIONS

(71) Applicants: James P. Horgan, West Chester, PA (US); Jeffrey A. Klang, West Chester, PA (US); Thomas W. Hazell, Coatesville, PA (US); Yuhong He, Honey Brook, PA (US)

(72) Inventors: James P. Horgan, West Chester, PA (US); Jeffrey A. Klang, West Chester, PA (US); Thomas W. Hazell, Coatesville, PA (US); Yuhong He, Honey Brook, PA (US)

(73) Assignee: Arkema France, Colombes (FR)

( * ) Notice: Subject to any disclaimer, the term of this patent is extended or adjusted under 35 U.S.C. 154(b) by 89 days.

(21) Appl. No.: 13/644,483

(22) Filed: Oct. 4, 2012

(65) Prior Publication Data
US 2013/0090444 A1 Apr. 11, 2013

Related U.S. Application Data

(60) Provisional application No. 61/543,613, filed on Oct. 5, 2011.

(51) Int. Cl.
*C08F 26/02* (2006.01)
*C08F 118/02* (2006.01)
*C07C 229/30* (2006.01)
*C08K 3/00* (2006.01)

(52) U.S. Cl.
USPC ....... 526/312; 526/319; 560/170; 252/183.11

(58) Field of Classification Search
USPC ............... 526/312, 319; 560/170; 252/183.11
See application file for complete search history.

(56) References Cited

U.S. PATENT DOCUMENTS

| | | | |
|---|---|---|---|
| 6,552,103 B1 | 4/2003 | Bertozzi et al. | |
| 7,094,349 B2 | 8/2006 | Inoue et al. | |
| 2002/0052465 A1 | 5/2002 | Fleet et al. | |
| 2005/0164963 A1 | 7/2005 | Essler et al. | |
| 2010/0092782 A1 | 4/2010 | Perrier et al. | |
| 2010/0129755 A1 | 5/2010 | Hendrikx et al. | |
| 2011/0009641 A1 * | 1/2011 | Anderson et al. | 548/340.1 |
| 2011/0154583 A1 | 6/2011 | Lewis et al. | |

FOREIGN PATENT DOCUMENTS

| | | |
|---|---|---|
| JP | 5 148288 | 6/1993 |
| JP | 10 142757 | 5/1998 |
| WO | WO 03/068377 | 8/2003 |
| WO | WO 03068377 A1 * | 8/2003 |
| WO | WO 2009/043900 | 4/2009 |

OTHER PUBLICATIONS

PCT/EP12/069642 (Search Report), Apr. 10, 2012, Arkema France.
Piasecki, A., et al., "Method for N-[2-alkoxycarbonylethyl]-N-alkyl-1-amino-1-deoxy-D-glucitols", Chemical Abstracts Service, Columbus, Ohio, US, Dec. 31, 2010.
Bordege, V., et al., "Glycopolymers with glusamine pendant groups: Copolymerization, physico-chemical and interaction properties", Reactive & Functional Polymers, Elsevier Science Pub BV, NL, vol. 71, No. 1, Nov. 11, 2010, pp. 1-10.
Gill, H.S., et al., "Soft beta-adrenergic agonists for the topical treatment of psoriasis", European Journal of Medicinal Chemistry, Editions Scientifique Elsevier, Paris, FR, vol. 31, No. 11, 1996, pp. 847-859.
Dokichev, T.V., et al., "Synthesis of N-(2-hydroxyethyl) derivatives of beta-alamine". Doklady Chemistry, Maik Nauka/Internperiodica Publishing, Moscow, RU, vol. 430, No. 2, Jan. 1, 2010, pp. 47-49.
Mathias, L.J., et al, May 1, 2004, "Synthesis of New Hydroxylated Monomers Based on Methacrylate Dimethacrylate & Tetramethacrylate Michael Adducts and Photopolymerization Kinetics of Bulk Cross-Linkers" Macromolecules vol. 37 No. 9.

\* cited by examiner

*Primary Examiner* — Michael M Bernshteyn
(74) *Attorney, Agent, or Firm* — Lynn B. Morreale

(57) ABSTRACT

A compound which is the Michael addition reaction product of (A) a mono or polyacrylate of the formula $R^1(Ac)_n$ wherein $R^1$ is an organic radical having at least 2 carbon atoms, Ac is an acrylate radical of the formula $CH_2=CHC(O)O-$, and n is from at least 1; with (B) is a primary or secondary amine of the formula $R^2NHR^3$, wherein $R^2$ is a polyhydroxyl radical and $R^3$ is H or an organic radical having at least one carbon atom is disclosed. The compound is useful as, for example, an oxygen barrier, flame retardant, polymer flocculant, surfactant, and/or high hydroxyl-functional intermediate.

18 Claims, No Drawings

US 8,759,464 B2

POLAR, MULTI-HYDROXYL FUNCTIONAL AMINO COMPOUNDS, COMPOSITIONS, PROCESS FOR PREPARATION, THEIR USES AND APPLICATIONS

CROSS-REFERENCE TO RELATED APPLICATIONS

This application claims benefit to U.S. provisional application Ser. No. 61/543,613, filed Oct. 5, 2011, which is hereby incorporated by reference.

FIELD OF THE INVENTION

The present invention relates to polyhydroxyl amino compounds, reactions thereof, reaction products, and uses of the reaction products.

BACKGROUND OF THE INVENTION

Prior efforts to incorporate multi hydroxyl containing amino compounds, known as glycol amines or amino sugars, into polymer substances have been described by others. A few examples of such compounds are glucamine and alkyl glucamines, for example N-methyl glucamine (NMG), glucosamine, alkyl glucosamine and tris hydroxylmethyl amino ethane (THAM). Typically this is done by trying to synthesize glycol amine-functional reactive monomers that can be polymerized or alternately by modifying existing polymers to incorporate glycol amine functionality. The most common synthetic route is to attempt to react a glycol amine with epoxy functionality in an existing monomer or an epoxy functional polymer. The problem with such a route is that glycol amines and amino sugars are typically high melting point crystalline materials with poor solubility in any material other than water or very polar solvents. Modification steps are typically inefficient and difficult to arrange without proper reaction media. Also, in water or polar solvents, ring opening polymerization of epoxy groups is a very likely undesired side reaction competing with the desired selective single ring opening of epoxy by amino group.

Another method reported for synthesis of polymerizable amino sugar monomers is to react available amino groups with acryloyl chloride to form an acrylamide structure. One problem is that acryloyl chloride is not readily commercially available and is a strong lachrymator that is difficult and dangerous to store and handle.

Yet another method for incorporating amino sugars into reactive monomers or polymers is to use the amino group to neutralize carboxylic acid functions. In this case, the amino sugar is ionically incorporated into systems which may provide useful properties for some applications but is not optimal for others.

None of these methods are ideal nor are they the most desirable commercially to practice. Among the prior art methods are those disclosed in U.S. 2010/0092782, U.S. 2010/0129755, U.S. Pat. Nos. 6,552,103, and 7,094,349.

It is well known in the art that low molecular weight primary and secondary amine compounds, including hydroxylamine compounds, that are liquid or have low melting points and are soluble in acrylates may be readily reacted into acrylate compositions by Michael addition, to the alpha, beta unsaturation of a multifunctional acrylate monomer. However, an effective, solvent-free method of reacting crystalline solid amino sugars which have higher melting points and very limited or no apparent solubility in acrylate-functional materials with acrylate compounds has not been described in the prior art. There is a need in the art for such new products and a solvent-free method of preparation by reacting said crystalline multi-hydroxylamino compounds.

There is also a need for reactive monomer compositions which may be used as novel surfactants, preparing adhesives, sealants, and coatings, including, without limitation, UV curable compositions.

DESCRIPTION OF CERTAIN EMBODIMENTS OF THE INVENTION

This need is addressed by the present invention which comprises in one aspect a compound which is the reaction product, preferably the Michael addition reaction product, of (A) a mono or polyacrylate of the formula $R^1(Ac)_n$ wherein $R^1$ is an organic radical, with valency according to n, having at least 2 carbon atoms, Ac is an acrylate radical of the formula $CH_2$=CHC(O)O—, and n is at least 1, preferably from 1 to 16 and more preferably from 2 to 16; with (B) a primary or secondary amine of the formula $R^2NHR^3$, wherein $R^2$ is a polyhydroxyl radical, particularly with at least two and preferably at least 3 hydroxyl groups and $R^3$ is H or an organic radical having at least one carbon atom. The compound is useful as, for example, an oxygen barrier, flame retardant, polymer flocculant, surfactant, and/or high hydroxyl-functional intermediate. Such intermediates can be homopolymerized if they include ethylenic unsaturation such as methacrylate groups and used as coatings, resins, sealants, and adhesives, for example. The compound can be homopolymerized, copolymerized with other monomers, or grafted onto other polymers via free radical polymerization through the (meth)acrylate group(s).

In another aspect the invention comprises a method which comprises reacting (A) a mono or polyacrylate of the formula $R^1(Ac)_n$ wherein $R^1$ is an organic radical having at least 2 carbon atoms, Ac is an acrylate radical of the formula $CH_2$=CHC(O)O—, and n is at least 1; with (B) a primary or secondary amine of the formula $R^2NHR^3$, wherein $R^2$ is a polyhydroxyl radical and $R^3$ is H or an organic radical having at least one carbon atom under Michael addition conditions in the absence of solvent wherein the resultant compound is water soluble. Preferably the reaction temperature is maintained below about 125° C., preferably from 60° C. to less than 125° C. and more preferably from 90° C. to less than less than 125° C. while substantially avoiding free radical polymerization.

We have discovered that amino sugars which are solids, preferably crystalline solids, that have limited or no apparent solubility in acrylate-functional materials and typically have melting points higher than the temperatures where acrylate compounds have reliable stability and do not autopolymerize, may be effectively added, without use of solvent or water, directly to acrylate moieties in diacrylate, triacrylate, tetracrylate or higher as well as mixed acrylate/methacrylate and other mixed acrylate/functional group compositions, presumably via Michael addition of the basic nitrogen group to acrylate double bond. This method allows a simple and economic method for preparing polymerizable acrylate, (meth) acrylate, or other reactive functional compositions which contain amino sugar moieties. Normally, these compositions are water soluble for use in aqueous compositions or they may be used in various applications by themselves or combined with other components to make curable coatings, polymers or other compositions with useful properties.

Additionally, amino sugars may be added directly to acrylate compounds to yield final products which may be useful as novel reactive or non-reactive surfactants or in water dispersion applications. Also, amino sugars may be added to acrylate compounds to prepare new types of polyols with hydroxyl content, preferably high hydroxyl content, to control reactivity or properties in traditional cure systems using hydroxy components.

In some embodiments an amino sugar (B) with a single secondary amine group, such as NMG (N-methyl glucosamine), which contains a single reactive proton is added one equivalent per acrylate function of the (A) compound. Amino sugars with multiple secondary amine groups or with primary amine groups may react with multiple acrylate equivalent groups. By selection of the appropriate amino sugar and acrylate components, one can design a wide array of components or polymer structures (such as, for example, ABAB type linear oligomers and polymers or gelled structures or star structures). For example, THAM (tris hydroxymethyl aminomethane) has the potential to prepare ABAB type repeating oligomeric structures with diacrylates or may be reacted with two monoacrylate molecules to adjust surfactant properties.

In some embodiments (B) is selected from N-substituted or unsubstituted glucamine, for example the above-mentioned NMG, N-substituted or unsubstituted glucosamine, and N-substituted or unsubstituted tris hydroxymethyl aminomethane (THAM), and combinations or mixtures thereof.

The organic radical $R^1$ can be, in certain embodiments, (a) an alkyl or substituted alkyl group having 4-20 carbon atoms, particularly with a valency according to n; or (b) radical derived from the reaction product of glycidyl methacrylate and acrylic acid and having the formula $CH_2=C(CH_3)C(=O)OCH_2CH(OH)CH_2$— with valency n being 1. The methacrylic unsaturation, in contrast to the behavior of the acrylic one, is unaffected by the Michael addition reaction between acrylate and the amino groups.

Preferably the alkyl or substituted alkyl group has 4-20 carbon atoms. One preferred example of alkyl is lauryl $R^1$ can also be a radical derived from unsubstituted and substituted cyclic and multicyclic hydrocarbon, unsubstituted and substituted heterocyclics, unsubstituted and substituted aromatics, and combinations thereof. In some embodiments $R^1$ includes one or more free radical (or free radically-) polymerizable groups other than acrylate groups, examples of which (other than acrylate) are methacrylate, vinyl and allyl groups, preferably methacrylate and vinyl groups. $R^1$ may also comprise a hydroxyl group.

The equivalents ratio based on acrylate groups Ac, and N—H groups (Ac/N—H) of (A) to (B) can vary but is generally about 0.5/1 to 16/1, preferably 1/1 to 4/1. The ratio may be lower or equal to 1 and in such a case it corresponds to compounds without residual acrylate groups. Such compounds are particularly suitable for use as non ionic surfactants or dispersants for aqueous media. It is also possible with a ratio lower or equal to 1, to obtain compounds of the invention without remaining residual acrylate group Ac but bearing in R1, at least one ethylenically unsaturated group, free radically-polymerizable initially beared by radical R1 and kept unaffected by Michael addition reaction, these groups being selected from methacrylate, vinyl or allyl and preferably methacrylate or vinyl groups. According to another possibility, the said ratio is higher than 1 and more particularly n is of at least 2. This case does particularly correspond to compounds bearing at least one residual acrylate group Ac, which is free radically-polymerizable. In addition to the at least one free radically-polymerizable acrylate group, the compound of the invention in this case (ratio>1) may additionally (to at least one acrylate Ac) comprise at least one other polymerizable group like methacrylate, vinyl or allyl and preferably methacrylate or vinyl which group is comprised in said radical R1. Even more particularly for compounds having at least one free-radically-polymerisable acrylate group, the said ratio may range from 2/1 to 16/1, preferably from 2/1 to 4/1.

Consequently the compounds of the present invention, which are suitable for free radical polymerization, bear at least one free radically-polymerizable group selected from at least one residual Ac acrylate group (when ratio Ac/NH>1) and/or at least one group derived from R1 which is methacrylate, vinyl or allyl, preferably methacrylate or vinyl. If Ac/NH≤1 then only polymerizable groups derived from R1 can be present in the final product (if said group is present in R1).

Among the various embodiments of the compounds are those wherein (A) with functionality n in acrylate groups as defined above, is an acrylate ester of alcohols, such as: ethanol, propanol, isopropanol, butanol, isobutanol, hexanol, methyl pentanol, iso-octanol; n-octanol; 2-ethylhexanol, isodecanol; n-decanol; lauryl alcohol; tridecyl alcohol; tetradecyl alcohol; cetyl alcohol; stearyl alcohol; behenyl alcohol; cyclohexyl alcohol; 3,3,5-trimethyl cyclohexyl alcohol; cyclic trimethylolpropane formal; 2-phenoxy ethanol; nonyl phenol, isobornol; and (meth)acrylate esters of diols and polyols such as ethylene glycol; propylene glycol; 1,3 propane diol; 1,3 butane diol; 1,4 butane diol; 1,6 hexanediol; 3-methyl-1,5-pentanediol; 1,9-nonanediol; 1,10-decanediol, 1,12-dodecanediol; 1,4-cyclohexanedimethanol; tricyclodecanedimethanol; neopentyl glycol; trimethylol propane; glycerol; tris(hydroxyethyl)isocyanurate; pentaerythritol; di-trimethylolpropane; di-pentaerythritol; and alkoxylated or caprolacatone modified derivatives of such alcohols, diols and polyols; dipropylene glycol; tripropylene glycol and higher polypropylene glycols; diethylene glycol; triethylene glycol; tetraethylene glycol and higher polyethylene glycols; mixed ethylene/propylene glycols; and alkoxylated bis-phenol A derivatives, acrylate or diacrylate of glycidyl methacrylate, acrylate of allylic alcohol or of alcoxylated allylic alcohol, acrylate of vinyl alcohol, or acrylates of hydroxyalkyl methacrylates, ethoxylated trimethylolpropane triacrylate (ethoxylated TMPTA), glycerol triacrylate or diacrylate, trimethylol propane triacrylate (TMPTA), hexanediol diacrylate, bisphenol A diacrylate, phenoxy ethyl acrylate, ethoxylated nonyl phenol acrylate.

In yet other embodiments of the compounds are those wherein (A) may be oligomers, bearing n acrylate groups as defined above, selected from the group consisting of:
  epoxy (meth)acrylates, such as those derived from an ether selected from the group consisting of bis-phenol A diglycidyl ether 1,4-butanediol diglycidyl ether or polypropylene glycol diglycidyl ether;
  urethane (meth)acrylates such as those derived from an isocyanate selected from the group consisting of toluene diisocyanate methylene diphenyl diisocyanate hydrogenated methylene diphenyldiisocyante isophorone diisocyanate hexamethylene diisocyanate trimethyl hexamethylene diisocyanate in combination with an active hydrogen compound selected from the group consisting of a polyester, polyether or polycarbonate polyol; hydroxyalkyl(meth)acrylate such as hydroxyethyl (meth)acrylate or polycaprolactone (meth)acrylate; and
  polyester acrylates derived from di or poly-hydroxy compounds and di or poly-carboxylic acid functional compounds.

(A) may also include dendritic acrylates, such as those marketed by Sartomer USA, LLC as CN2301, CN2302, CN2303 and CN2304.

Another form of oligomeric acrylates may include multifunctional acrylated acrylic oligomers derived from glycidyl methacrylate, such as those derived from the complete or partial acrylation by acrylic acid of epoxy groups of a copolymer of glycidyl methacrylate with at least another acrylic comonomer, for example an acrylated oligomer of methyl methacrylate with of glycidyl methacrylate.

The term (meth)acrylate or (meth)acrylates as used in the above list means: either acrylates or mixed methacrylate with acrylates in the same compound A.

Specifically, (A) may also be a compound of the formula (I)

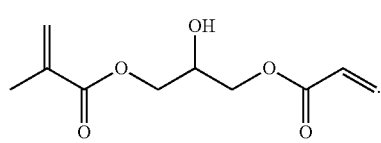
(I)

Examples of compounds prepared by the methods of the invention are those comprising, or consisting essentially of, or consisting of, a product of the structure/formula (I-a), (I-b), and (I-c) as follows:

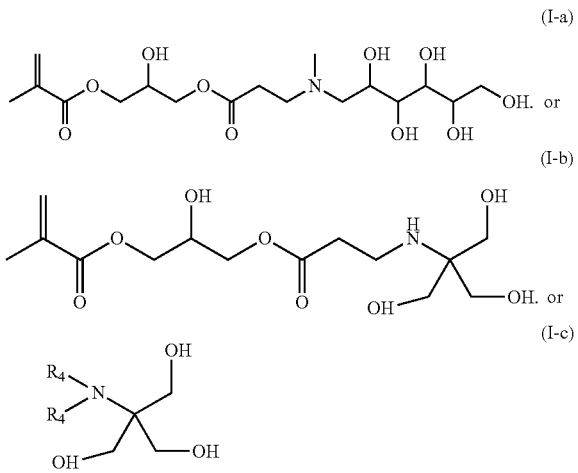
(I-a)

(I-b)

(I-c)

where (in I-c), $R_4$ is defined as follows:

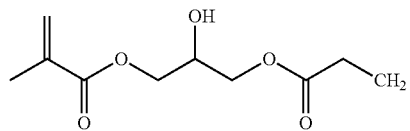
(R4)

In a preferred embodiment of the present invention, amine (B) is N-methyl-d-glucamine (NMG) of the structure/formula (II-a)

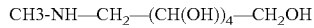
CH3-NH—CH$_2$—(CH(OH))$_4$—CH$_2$OH (II-a)

or it is tris hydroxymethyl amino methane (THAM) of the structure/formula (II-b)

NH$_2$C(CH$_2$OH)$_3$ (II-b).

In another preferred embodiment, (A) is ethoxylated trimethylol propane triacrylate (ethoxylated TMPTA), particularly with a molar ratio of (A) to (B), such that the ratio Ac/NH>1, preferably is 1.5/1 or higher, more preferably higher than 2/1, with (B) preferably being according to the above formula (II-a) or (II-b) as defined above.

It is preferred that the Michael addition reaction is carried out in the absence of a solvent and the resulting compounds of the invention are water-soluble. In some preferred embodiments the method comprises the step of maintaining the reaction temperature below about 125° C. and substantially avoiding any free radical polymerization.

The chemistry and compositions can be used directly or in polymers for a wide array of applications such as an oxygen barrier, flame retardant, polymer flocculant, surfactant and particularly as non ionic surfactant, as boron fixation agent for water treatment, or preserving wood and/or as high hydroxyl-functional intermediate.

The compounds of the invention are useful for preparation of boron fixation polymers for wood preservation or for ion exchange polymers used to remove boron in water treatment applications and other applications where boron fixation and removal is beneficial.

The compounds of the invention are also useful for the preparation of hydrogel polymers for various applications including biomedical or medical devices, coatings for antistat (antistatic) properties, in paper coatings as to provide a hydrophilic surface for printing, as anti-fog coatings, as wet adhesion promoters, as fire retardant (intumescent) agents, as oxygen gas barriers, as adhesion promoters in coatings on glass, metal and other polar surfaces, as water soluble resins in curable inks and coatings, as specialty crosslinkers imparting hydrophilic or both hydrophilic and hydrophobic character to polymers such as in superabsorbing polymers or as water developable photopolymers.

More particularly, NMG provides pharmaceutical properties so the compositions of this invention may be used in polymers for medical or pharmaceutical applications, reactive components to be incorporated into other compositions to provide water dispensability, inert non-ionic surfactants, and specialty polyols for incorporating into isocyanate or other cure systems.

In all cases where acrylate-functionality is at least partially retained, the compositions may be cured into coatings, adhesives, sealants, and polymer substances by free radical mechanisms (including UV, electron beam or peroxide initiated systems). Additionally, in cases where acrylate-functionality is retained, the composition may be used in modified two part (or two components or 2k) epoxy-amine cure systems, as they can react with curative amine component and provide enhanced performance.

Unexpectedly, the solid crystalline amino sugars such as NMG or THAM may be reacted directly without use of any solvent or other medium (unless desired to reduce eventual viscosity) and converted to acrylate groups by stirring at relatively mild temperatures such as 60° C. to less than 125° C. This is particularly surprising as NMG has a high melting point temperature of 130° C. and THAM has an even higher melting point at greater than 175° C. Normally, acrylate or methacrylate containing compositions are not thermally stable against undesired polymerization at such high temperatures, and so it is particularly useful to find that these materials, despite their very poor solubility, may be reactively added to acrylate groups at below 125° C., preferably at 60° C. to below 125° C. temperature range.

One of the subjects of the present invention is a method of preparation of a compound as defined above according to the invention, where it comprises a reaction, preferably a Michael addition reaction, of amine (B) with said mono or polyacrylate (A), by a progressive addition and reaction of (B) on (A)

in the absence of any solvent at a temperature below 125° C., preferably from 60° C. to less than 125° C., more preferably from 90 to less than 125° C., with the obtention of a water-soluble compound and more preferably without substantial free radical polymerization. "Without substantial free radical polymerization" means the absence of free radical polymerization which could be thermally initiated whereby conditions are controlled to avoid such a thermal polymerization. For example, thermal polymerization may be avoided by controlling temperature and adding stabilizers against thermal polymerization. Free radical scavenger stabilizers are well-known to those skilled in the art.

Compounds of the invention, when containing at least one polymerizable group, may be used in the preparation of a polymer or of an oligomer. This can be done by free radically polymerizing said compound, to obtain a homopolymer, or by a copolymerizing said compound, particularly with another convenient comonomer to obtain a copolymer. The polymer or oligomer may be grafted or crosslinked. More particularly, the crosslinked polymer or oligomer is obtained from a compound which bears at least two free radically polymerizable groups or/and in the presence of a free radical crosslinker. Said free radical crosslinker preferably bears at least two ethylenically unsaturated polymerizable groups.

In another preferred embodiment, the compound of the invention has two residual Ac acrylate groups and is a diacrylate compound according to the invention. In this case, linear polymer or oligomer may be also obtained from said compound of the invention by successive Michael addition reactions of convenient diamines, such as primary monoamine or a secondary amine diamine, with the compound of the invention having the diacrylate structure. So, the linear polymer or oligomer according to this embodiment, is a Michael polyaddition reaction product of a primary monoamine or a secondary amine diamine, with said compound of the invention (diacrylate compound), and optionally said polymer or oligomer may be an acrylated linear polymer or oligomer with terminal acrylate groups. More particularly with an excess of acrylate groups of said compound to amine (NH) groups of the amine (primary monoamine or diamine with secondary amine groups) the said linear oligomer or polymer will be a diacrylate-ended to corresponding linear oligomer or polymer (acrylated linear poyadduct of Michael polyaddition reaction).

A crosslinked polymer may be a two part (or two components or 2k) epoxy/amine cured polymer, derived from a two-components or 2k curable epoxy-amine composition comprising the compound according to the invention.

In another preferred embodiment, the cross-linked polymer of the invention is a hydrogel polymer. This means that it may be crosslinked polymer comprising or swollen by water. Such hydrogels may have medical or pharmaceutical applications.

The present invention also provides additional uses of the compounds of the present invention. For example these compounds may be used in the preservation of wood, particularly, for example, a method comprising a step of applying a complex or mixture of boron and said compounds of the invention to the wood.

Another potential use of a compound as defined according to the invention relates to its use as an oxygen barrier, as a flame retardant agent, as a polymer flocculant, as a surfactant and particularly as a non-ionic surfactant, as a monomer for polymers or oligomers or resins, as a monomer for hydrogels, as a monomer for preparing boron-complexing ion exchange resins, and/or as a high hydroxyl-functional intermediate for chemical synthesis.

More particularly, grafted homopolymers and copolymers obtained from compounds of the invention, may be used as polymeric dispersants, preferably for polymeric aqueous dispersions of hydrophobic polymers, resins or oligomers.

The following examples are presented for purposes of illustration of the present invention and of the related performances. These examples do not at all limit the scope and the covering of the claimed invention.

EXAMPLES

Example 1

Preparation of a Mono Methacrylate Monomer Incorporating NMG in its Structure

Acrylated glycidyl methacrylate is prepared by reacting glycidyl methacrylate (GMA) via the epoxy group with an equivalent amount of acrylic acid through ring opening addition to yield an intermediate composition (acrylated GMA) containing both a methacrylate and acrylate functional group. The intermediate composition (product) is heated to 80° C. and a molar equivalent of N-methyl-D-glucamine (Aldrich Chemical) NMG solid (1 N—H per acrylate Ac) is added in portions over two to three hours. Surprisingly, the NMG reacts into the liquid and final clear, semi-viscous liquid product is obtained with chromatographic profile and NMR spectra showing selective addition of NMG across the acrylate group. The final composition is useful "as is" or is easily diluted with water in any proportion. It is fully miscible with water.

Example 2

Preparation of an NMG-Modified Multifunctional Acrylate

One mole of ethoxylated trimethylolpropane triacrylate (3EO-TMPTA), SR454 brand, Sartomer Company, is heated to 80° C. and 1.3 moles of NMG (Ac/N-H:2.3) are added in portions and reactively incorporated into the composition at 95° C. to 100° C. over three hours to yield a clear, viscous liquid of 4,400 mPa·s (cP) at 70° C. product, with active NMG moieties and an average number of polymerizable acrylate groups per molecule of 1.7. The product was used neat for use in applications such as UV/EB curable inks or coatings. The product was also used in polymer synthesis or in peroxide cure, thermal cure, or epoxy/amine cure inks and coatings. Alternatively, the composition was diluted with water for use in aqueous applications.

Example 3

Preparation of a Mono Methacrylate Monomer Incorporating THAM in its Structure from Acrylated Glycidyl Methacrylate (Intermediate) of Example 1.

Acrylated glycidyl methacrylate (as disclosed in example 1) was heated with stirring at 120° C. and 1 mole equivalent of THAM (Ac/N—H, 0.5/1) was added in portions and the mixture was reacted for 1 hour at 120° C. to yield a clear, stable liquid product, with viscosity of 8,500 mPa·s (cP) at 60° C. Conversion of the acrylate of glycidyl methacrylate was 98% as measured by HLPC analysis.

Example 4

Preparation of a Mono/Di Methacrylate Monomer Composition Incorporating THAM in its Structure from Acrylated Glycidyl Methacrylate (Intermediate) of Example 1.

Acrylated glycidyl methacrylate (as disclosed in example 1), 1.6 moles, was heated with stirring at 120° C. and 1 mole equivalent of THAM (Ac/N—H, 0.8/1) was added in portions and the mixture was reacted for 3.5 hours at 120° C., to yield a clear, stable liquid product, with viscosity of 7,300 mPa·s (cP) at 60° C. Conversion of the acrylate of glycidyl methacrylate was 95% as measured by HLPC analysis. The resulting product provides a mixture of a mono-methacrylate monomer and dimethacrylate functional monomer. The product is dispersible in water.

Example 5

Preparation of a Diacrylate Linear Oligomer Composition Incorporating THAM from a Diacrylate Two moles of tetraethylene glycol diacrylate, SR268 brand, Sartomer Company, is heated to 120° C. and 1 mole of tris hydroxy methyl amino methane (THAM) solid is added in portions over an hour (Ac/N—H: 2/1), reactively incorporated into the composition and allowed to cool to room temperature to yield a stable, clear liquid product with active multihydroxyl groups and reactive acrylate functionality. The product was used neat for use in applications such as UV/EB curable inks or coatings. The product was also used in polymer synthesis or in peroxide cure, thermal cure, or epoxy/amine cure inks and coatings. Alternatively, the composition was diluted with water for use in aqueous applications.

Example 6

Preparation of an Inert, Non-Ionic Surfactant Composition Using NMG

One mole of lauryl acrylate, SR335 brand, Sartomer Company, is heated to 115° C. and one mole of NMG solids (Ac/N—H: 1/1) are added in portions and the mixture is agitated for 1.5 hours at 115° C. until a clear liquid reaction mass is achieved. Upon cooling, the novel composition with both hydrophilic and hydrophobic moieties, crystallizes to a solid (melting point of 63° C.-64° C.) which is dispersible in water and provide surfactant properties, like foaming.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

The invention claimed is:

1. A compound which is the reaction product of (A) a mono or polyacrylate of the formula $R^1(Ac)_n$, wherein $R^1$ is an organic radical having at least 2 carbon atoms, Ac is an acrylate radical of the formula $CH_2$=CHC(O)O—, and n is at least 1; with (B) a primary or secondary amine of the formula $R^2NHR^3$, wherein $R^2$ is a polyhydroxyl radical and $R^3$ is H or an organic radical having at least one carbon atom, wherein (B) is one or more selected from the group consisting of N-substituted or unsubstituted glucamine, N-substituted or unsubstituted glucosamine, and N-substituted or unsubstituted tris hydroxymethyl aminomethane.

2. The compound according to claim 1, wherein the reaction product is a Michael addition product.

3. The compound according to claim 1, wherein n is from 1 to 16.

4. The compound according to claim 1, wherein $R^1$ is selected from the group consisting of (a) an alkyl or substituted alkyl group having 4-20 carbon atoms and (b) the reaction product of glycidyl methacrylate and acrylic acid and having the formula $CH2$=$C(CH3)C(O)OCH2CH(OH)CH2$—.

5. The compound according to claim 1, wherein $R^1$ is an alkyl.

6. The compound according to claim 1, wherein $R^1$ is selected from the group consisting of radical derived from unsubstituted and substituted cyclic and multicyclic hydrocarbon, unsubstituted and substituted heterocyclics, unsubstituted and substituted aromatics, and combinations thereof.

7. The compound according to claim 1, wherein $R^1$ includes at least one free radical polymerizable group other than acrylate, selected from the group consisting of methacrylate, vinyl, and allyl.

8. The compound according to claim 1, wherein $R^1$ is an organic radical comprising a hydroxyl group.

9. The compound according to claim 1, wherein the equivalents ratio based on acrylate groups Ac, and N—H groups (Ac/N—H) of (A) to (B) is from 0.5/1 to 16/1.

10. The compound according to claim 9, wherein said ratio is 0.5 to 1.

11. The compound according to claim 9, wherein said ratio is from 1/1 to 16/1.

12. The compound according to claim 1, wherein (A) is selected from the group consisting of: (a) acrylate esters of alcohols, (b) (meth)acrylate esters of diols and polyols, and (c) alkoxylated or caprolactone modified derivatives of mono-ols, diols and polyols.

13. The compound according to claim 1, wherein (A) is an oligomer selected from the group consisting of: (a) epoxy (meth)acrylate (oligomers) derived from an ether selected from the group consisting of bis-phenol A diglycidyl ether, 1,4-butanediol diglycidyl ether, and polypropylene glycol diglycidyl ether; (b) urethane methacrylates derived from an isocyanate selected from the group consisting of toluene diisocyanate, methylene diphenyl diisocyanate, hydrogenated methylene diphenyldiisocyante, isophorone diisocyanate, hexamethylene diisocyanate, or trimethyl hexamethylene disocyanate in combination with a compound selected from the group consisting of polyester, polyether, and polycarbonate polyols, and hydroxyalkyl(meth)acrylates (c) polyester acrylates derived from di or poly-hydroxy compounds and di or poly-carboxylic acid functional compounds, (d) dendritic acrylates, and (e) multifunctional acrylated acrylic oligomers derived from copolymers of glycidyl methacrylate.

14. The compound according to claim 1, wherein (A) is a compound having structure (I):

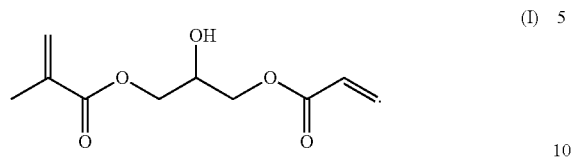

15. The compound according to claim 1, wherein amine (B) is N-methyl-d-glucamine having formula (II-a):

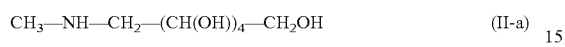

or tris hydroxy methyl amino methane having formula (II-b)

16. The compound according to claim 15, wherein (A) is ethoxylated trimethylol propane triacrylate, having a molar ratio of (A) to (B) such that Ac/N—H is from 1/1 to 16/1.

17. The compound according to claim 1 prepared by a method comprising a step of maintaining reaction temperature below about 125° C.

18. A compound as defined according to claim 1, having at least one free radically-polymerizable group selected from at least one residual Ac acrylate group and/or at least one group derived from R1 which is methacrylate, vinyl or allyl.

* * * * *